(12) United States Patent
MacAlpine et al.

(10) Patent No.: US 6,825,343 B2
(45) Date of Patent: Nov. 30, 2004

(54) 1,3-DIPOLAR CYCLOADDITIONS TO POLYPYRROLIC MACROCYCLES

(75) Inventors: Jill Kirsten MacAlpine, Alexandria, VA (US); Ethan D. Sternberg, Vancouver (CA); David Dolphin, Vancouver (CA)

(73) Assignee: University of British Columbia, Vancouver (CA)

( * ) Notice: Subject to any disclaimer, the term of this patent is extended or adjusted under 35 U.S.C. 154(b) by 0 days.

(21) Appl. No.: 10/622,322

(22) Filed: Jul. 17, 2003

(65) Prior Publication Data

US 2004/0019201 A1 Jan. 29, 2004

Related U.S. Application Data

(63) Continuation of application No. 09/551,160, filed on Apr. 14, 2000, now Pat. No. 6,620,929.
(60) Provisional application No. 60/129,324, filed on Apr. 14, 1999.

(51) Int. Cl.$^7$ ............................................. C07D 487/22
(52) U.S. Cl. ........................................................ 540/145
(58) Field of Search ......................................... 540/145

(56) References Cited

U.S. PATENT DOCUMENTS

| | | | | |
|---|---|---|---|---|
| 4,883,790 A | 11/1989 | Levy et al. | ................. | 540/145 |
| 4,920,143 A | 4/1990 | Levy et al. | ................. | 514/410 |
| 5,095,030 A | 3/1992 | Levy et al. | ................. | 514/410 |
| 5,171,749 A | 12/1992 | Levy et al. | ................. | 514/410 |
| 5,283,255 A | 2/1994 | Levy et al. | ................. | 514/410 |
| 5,399,583 A | 3/1995 | Levy et al. | ................. | 514/410 |
| 5,648,485 A | 7/1997 | Dolphin et al. | ............ | 540/474 |
| 5,726,304 A | 3/1998 | Tang et al. | ................. | 540/145 |
| 5,990,149 A | 11/1999 | Sternberg et al. | ........... | 514/410 |
| 6,620,929 B1 * | 9/2003 | MacAlpine et al. | ........ | 540/145 |

FOREIGN PATENT DOCUMENTS

WO    WO 96 13504    5/1996

OTHER PUBLICATIONS

Faustino, M.S.F. et al. (1996). "Diels–Alder Reactions of Ni(11)β–Vinyl–meso–Tetraarylporphyrins," *Tetrahedron Lett* 37(20):35693570.

Huisgen, R. (1963). "1,3–Dipolare Cycloadditionen;" *Angew Chem* 75:604–637.

Huisgen, R. (1968). "Cycloadditionen—Begriff, Einteilung und Kennzeichnung," *Angew Chem* 80:329–337.

Huisgen, R. (1961). "1,3–Dipolar Cycloadditions," *Proc Chem Soc*: 357–369.

Kaufmann, T. (1974). "1,3–Anionic Cycloadditions of Organolithium Compound: An Intitial Survey," *Angew Chem Int Ed Engl* 13:627–639.

Linn, W.J. et al. (1965). "Tetracyanoethylene Oxide. 1.Preparation and Reaction with Nucleophiles," *J Am Chem Soc* 87:3651–3656.

Linn, W.J. et al. (1965). "Tetracyanoethylene Oxide. 11.Addition to Olefins, Acetylenes, and Aromatics," *J Am Chem Soc* 87:3657–3656.

Linn, W.J. et al. (1965). "Tetracyanoethylene Oxide. 111. Mechanism of the Addition of Olefins," *J Am Chem Soc* 87:3665–3672.

Linn, W.J. et al. (1969). "Tetracyanoethylene Oxide. 1Y. Nucleophilic Ring Opening," *J Org Chem* 34:2146–2152.

Lown, J.W. et al. (1972). "Reactions of Tetrasubstituted Azomethyne Ylides Generated from Tetracyanoethylene Oxide," *Can J Chem* 50:534–542.

Shea, K.M. et al. (1998). Dodecasubstituted Metallochlorines (metallohydroporphyrins). *J Chem Soc., Chem Comm:* 759–760.

Sisemore, M.F. et al. (1997). "Metalloporphyrin Peroxo Complexes of Iron(III), Manganese(III), and Titanium(IV), Comparative Studies Demonstrating that the Iron(III) is Extremely Nucleophilic," *Inorg Chem* 36:979–984.

Smith, K.M. et al. (1990). "Synthesis of Oxygen Analogues of the Sulfchlorins," *Tetrahedron Lett* 31(27):3853–3856.

Stuckwisch C.G. (1973). "Azomethyne Ylids, Azomethyne Imines, and Iminophosphoranes in Organic Synthesis," *Synthesis:* 469–483.

Tome, A.C. (1997). "Meso–Arylporphyrines as Dienophiles in Diels–Alder Reactions: A Novel Approach to the Synthesis of Chlorins, Bacteriochlorins and Naphthoporphyrins,"*J Chem Soc., Chem Comm:* 1199–1200.

Van Lier. (1991). "Photosensibilization: Reaction Pathways," *Photobiological Techniques* 216:85–98.

* cited by examiner

*Primary Examiner*—Richard L. Raymond
*Assistant Examiner*—Kahsay Habte
(74) *Attorney, Agent, or Firm*—Morrison & Foerster LLP

(57) ABSTRACT

Methods of modifying polypyrrolic macrocycles by use of a 1,3-dipolar cycloaddition is described. The methods may be used to produce compounds for further derivatization to produce photosensitizing agents of interest.

20 Claims, 6 Drawing Sheets

(213)

(214)

(1)

(2)

1,3-DIPOLAR CYCLOADDITIONS TO POLYPYRROLIC MACROCYCLES

RELATED APPLICATIONS

This application is a continuation of U.S. patent application Ser. No. 09/551,160, filed Apr. 14, 2000 now U.S. Pat. No. 6,620,929, which claims benefit of priority from U.S. Provisional application Ser. No. 60/129,324, filed Apr. 4, 1999, both of which are hereby incorporated by reference as if fully set forth.

FIELD OF THE INVENTION

The field of invention is the design and synthesis of compounds, useful in photodynamic therapy and related applications of photoactive compound technology. In particular, the present invention relates to methods to modify polypyrrolic macrocycle compounds, such as porphyrins, via a 1,3-dipolar cycloaddition reaction to produce intermediates that may be further derivatized to produce unique polypyrrolic macrocycle derivatives. In particular, the invention relates to the use of the carbonyl ylide class of 1,3-dipoles to modify polypyrrolic macrocycle compounds and produce intermediates for further derivatization by conventional chemical reactions. The invention also relates to the resulting compounds as members of this class. The resultant polypyrrolic macrocycle derivatives produced via such intermediates are useful as:

photosensitizers for photodynamic therapy;

chelators for radionuclides;

MRI contrast agents (i.e., chelators for paramagnetic metals);

other biomedical uses; and technical uses for infrared absorbing dyes, such as imaging, data recording and printing.

BACKGROUND OF THE INVENTION

Photodynamic therapy (PDT) generally involves the administration of compounds that are capable of absorbing light, typically in the visible range, but also in the near ultraviolet, followed by irradiation of locations in the subject for which a toxic, modifying or inhibitory effect is desired. PDT was initially developed using hematoporphyrin and related compounds in the treatment of tumors, as it appeared that these compounds would "home" to locations containing rapidly dividing cells. The tumor could then be irradiated with light absorbed by the hematoporphyrin and destruction of the surrounding tissue resulted. PDT has since been shown to be useful for treatment of atherosclerotic plaques, restenosis, infections in the blood stream, rheumatoid arthritis, psoriasis and in the treatment of ocular conditions not necessarily limited to tumors.

U.S. Pat. No. 5,171,749 and patents issuing on related applications, U.S. Pat. Nos. 5,283,255; 5,399,583; 4,883, 790; 4,920,143; 5,095,030; and 5,990,149; all of which are incorporated herein by reference, describe and claim a class of photoactive compounds useful in PDT designated the monohydrobenzoporphyrins, or "BPDs." This class is obtained by Diels-Alder reaction of a mono- or disubstituted alkyne with protoporphyrin-IX and the resultant compounds can further be isomerized, reduced, and/or derivatized to obtain a large class of BPDs. As disclosed in these patents, a particularly useful subclass of this group results from hydrolysis or partial hydrolysis of the ester groups of the 2-carboxylethyl side-chains on rings C and D. Esterification as protection of these groups during the Diels-Alder reaction results in initial products which contain 2-carbalkoxyethyl groups. It was found that facile hydrolysis of these esters could readily be conducted, leaving any carbalkoxy groups associated with the Diels-Alder product obtained from a dicarbalkoxyalkyne virtually completely unhydrolyzed.

Another means of derivatizing porphyrin compounds by use of osmium tetroxide has been previously described in U.S. Pat. No. 5,648,485 issued Nov. 3, 1998, which is hereby incorporated by reference as if fully set forth.

There remains, however, a continuing need to improve PDT by the production of additional derivatives of known polypyrrolic macrocycle photosensitizers or by the use of improved methods of synthesizing known polypyrrolic macrocycle photosensitizers.

SUMMARY OF THE INVENTION

The methods and compounds of the invention provide particularly useful new additions to the repertoire of compounds useful in photodynamic therapy (PDT) as well as means to expand this repertoire in a methodical fashion. The methods of the invention take advantage of the ability to modify polypyrrolic macrocycles by the use of a 1,3-dipolar cycloaddition reaction (see Huisgen, R., Angew. Chem. 1963, 75, 604; Huisgen, R., Angew. Chem. 1968, 80, 329; and Huisgen, R., Proc. Chem. Soc. 1961, 357). These types of reactions have become prominent in organic chemistry due to the vast number of bonds that undergo transformations (see Bianchi, G.; et al. In The Chemistry of Functional Groups A; Patai, S. Ed., Interscience: New York, 1977, 369; Stuckwisch, C. G., Synthesis 1973, 469; and Kaufmann, T., Angew Chem. Int. Ed. Engl. 1974, 13, 627). A "1,3-dipole" is a species that is represented by a zwitterionic octet structure and undergoes 1,3-cycloadditions with a multiple-bond system, the "dipolarophile." The 1,3-dipolar cycloaddition is a [3+2→5] cycloaddition which normally forms a five-membered heterocyclic ring. The ring closure is effected by cyclic electron shifts which form two new $\sigma$ bonds at the expense of $\pi$ bonds. Over 18 different types of 1,3-dipoles have been employed in such reactions, presenting numerous possibilities for variation over and above the variety due to the wide diversity of the nature of the dienophile.

All 1,3-dipoles incorporate an onium center whose positive charge neutralizes the negative charge on one of the terminal atoms to form a heteroallyl anion which bears no net charge. Two of the four allylic $\pi$ electrons can be delocalized at the center atom. The terminal centers of the dipoles can be either nucleophilic or electrophilic—the key to the reactivity of all 1,3-dipoles.

Formally, there are two types of 1,3-dipoles: those in which the central atom is sp-hybridized and those whose central atom is sp2-hybridized. The later group have allyl anion type $\pi$ systems with four electrons in three parallel atomic $\pi$ orbitals perpendicular to the plane of the dipole. This type of 1,3-dipole is bent and the central atom can be oxygen, nitrogen or sulfur 1,3-Dipoles having an sp-hybridized central atom are referred to as propargyl or allenyl types. These are linear and the central atom is confined to nitrogen.

1,3-dipolar cycloadditions with tetraphenylporphyrins have been previously attempted with diazoacetate and diazomethane (see Smith, K. M., et al. Tetrahedron Lett. 1990, 31, 3853). Cavaleiro et al. have performed a number of Diels-Alder reactions with tetraphenylporphyrins (Faustino, M. A. F., et al. Tetrahedron Lett. 1996, 37, 3569; and Tomé, A. C., et al. J. Chem. Soc., Chem. Comm. 1997, 1199).

Cavaleiro et al. also reported the dienophile-like nature of meso-tetraphenylporphyrins (see Tomé above).

While at least eight different classes of 1,3-dipoles (carbonyl ylides, nitrile oxides, diazoalkanes, azides, azomethine ylides, nitrile ylides, nitrones and azomethine imines) are potentially reactive and/or reactive towards aromatic systems, the present invention is directed to the use of carbonyl ylides in the modification of polypyrrolic macrocycle photosensitizers. While any carbonyl ylide may be used in the practice of the invention, preferred ylides are those that result in the modification of a polypyrrolic macrocycle to contain one or more cyano groups.

In a preferred aspect, the invention is directed to the modification of a polypyrrolic macrocycle with a carbonyl ylide to produce an intermediate compound containing one or more cyano groups. Such groups can then be used as functionalities for further derivatization of the compounds to produce macrocycles of interest.

Preferred derivative macrocycles are represented by the formulas

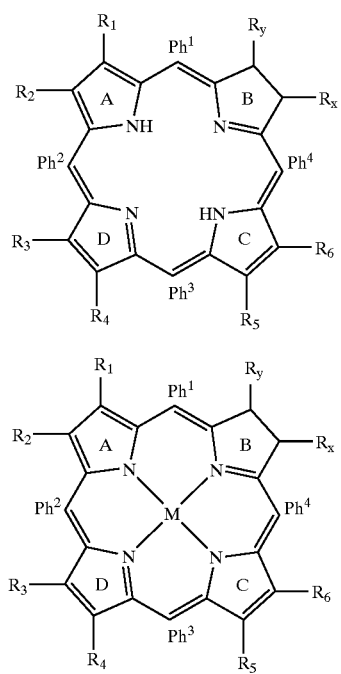

wherein formula I represents the structure of a polypyrrolic macrocycle of the invention and formula II represents the structure of the metallated form of the macrocycle. M is a metal selected from the group consisting of Ni(II), Cu(II), Zn(II), Fe(III)Cl, Sn, Ge, Si, Ga, Al, Mn(III), Gd(III), In and Tc;

$R_1$ through $R_6$ are independently a hydrogen atom, a lower alkyl group, a lower alkyl carboxylic acid or acid ester group, keto, hydroxy, nitro, amino or a group that, taken together with another ring, ring substituent or meso-substituent, forms a fused 5- or 6-membered ring.

Similarly, $R_x$ and $R_y$ are substituents formed from further derivatization of moieties introduced upon 1,3-dipolar cycloaddition to the macrocycle. Preferably, the cycloaddition results in a macrocycle intermediate containing one or more cyano groups. Upon further derivatization, $R_x$ and $R_y$ are independently selected from the group consisting of a hydrogen atom, a lower alkyl group, a lower alkyl carboxylic acid or acid ester group, keto, hydroxy, nitro, amino or a group that, taken together with another ring, ring substituent or meso-substituent, forms a fused 5- or 6-membered ring.

With respect to all $R_n$ groups, the other group covalently bonded to the carbon atom to which the $R_n$ is attached may be independently a hydrogen atom or a hydroxyl group.

$Ph^1$, $Ph^2$, $Ph^3$ and $Ph^4$ independently represent a group selected from H, substituted or unsubstituted alkyl groups, or substituted or unsubstituted aromatic rings, which may be the same or different.

Also included within the scope of the formulas are the salts and the metallated and/or labeled and/or conjugated forms thereof.

The invention is also directed to methods to make the compounds of the formula by modification of a base polypyrrolic macrocycle with a carbonyl ylide to form an intermediate which may then be subsequently isomerized, reduced, and/or derivatized.

Also included in the invention as a preferred embodiment are the intermediates and derivative compounds involved in the production of the formula and pharmaceutical compositions containing these compounds as well a methods to perform PDT using them.

BRIEF DESCRIPTION OF THE DRAWINGS

The present invention will be more clearly understood by referring to the following drawings, in which.

DETAILED DESCRIPTION OF THE INVENTION

The compounds of the invention are analogous to those set forth in U.S. Pat. No. 5,171,749 and its parents, U.S. Pat. Nos. 5,283,255; 5,399,583; 4,883,790; 4,920,143; and 5,095,030. The compounds of the invention differ from those set forth in these patents by virtue of their production by derivatization of intermediates produced by a 1,3-dipolar cycloaddition to the corresponding polypyrrolic macrocycle in either a metallated or non-metallated state.

Preferably, the cycloaddition of the invention is via use of a carbonyl ylide which produces a cyano containing intermediate that may be further derivatized. Alternatively, any suitable carbonyl ylide known in the art may be used in the present invention, but those that form an adduct are preferred. The availability of one or more cyano groups for further derivatization provides the special advantage of permitting the introduction of a carbon atom via production of a primary amine. This carbon atom introduction may be used to lengthen a carbon chain by one atom.

The ability to produce an amine also makes possible the further derivatization of the intermediate with the vast number of amine based reactions, including alkylation, amide formation, derivatization to a diazonium salt for subsequent replacement (e.g. by —Cl, —Br, —I, —CN, and —OH) or coupling, and imine formation.

Alternatively, the cyano containing moiety introduced into a polypyrrolic macrocycle may be base hydrolyzed to permit further derivatization. Such hydrolysis, for example, may be used to generate an acid and/or a carboxylate moiety that may be retained or further derivatized. Known chemistries of acids and carboxylates may be used in the production of other moieties, including α-alkylations, esters, amides, and thioamides.

The terms "intermediate" or "intermediate compound" are used to describe any compound of the invention that may be further derivatized to another compound. Such "intermediates" may be stable or unstable compounds under normal conditions and may or may not be photoactivatable. The terms also include compounds that may be suitable for use as photosensitizing agents with or without further derivatization.

Figure 1:
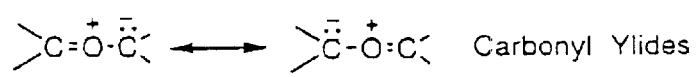
FIG. 1 shows the resonance structures of carbonyl ylides containing an oxygen center.
Figure 2:
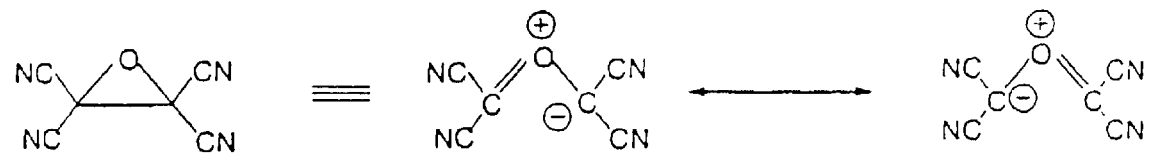
FIG. 2 shows the resonance structures of the carbonyl ylide tetracyanoethylene oxide (TCNEO).

In a preferred embodiment of the invention, the carbonyl ylide used is tetracyanoethylene oxide (TCNEO), which has been used with olefins, acetylenes and benzene at high temperatures (see Linn, W. J., et al. J. Am. Chem. Soc. 1965, 87, 3651; Lown, J. W., et al. Can. J. Chem. 1972, 50, 534; Linn, W. J., et al. J. Org. Chem. 1969, 34, 2146; Linn, W. J. et al. J. Am. Chem. Soc. 1965, 87, 3657; and Linn, W. J., et al. J. Am. Chem. Soc. 1965, 87, 3665). The products were those formed from [3 +2] cycloadditions with the carbonyl ylide. A first-order electrocyclic ring opening via cleavage of the carbon-carbon bond of the epoxide to the 1,3-dipole occurs (see Linn above). See FIG. 2. The TCNEO dipole adds cleanly to a variety of olefins, including aromatic substrates. Aromatic dipolarophiles include benzene, naphthalene, toluene, 1,3-cyclohexadiene and furan. These reagents produced the corresponding 1:1 adducts in 18-73% yields (Linn, W. J. et al. J. Am. Chem. Soc. 1965, 87, 3657).

For example, naphthalene reacts with one equivalent of TCNEO in 1,2-dibromoethane to give a single monoadduct at the 1,2-position in 73% yield after 4.75 hours. Polyaddition products were not produced even in the presence of excess TCNEO.

Figure 3:
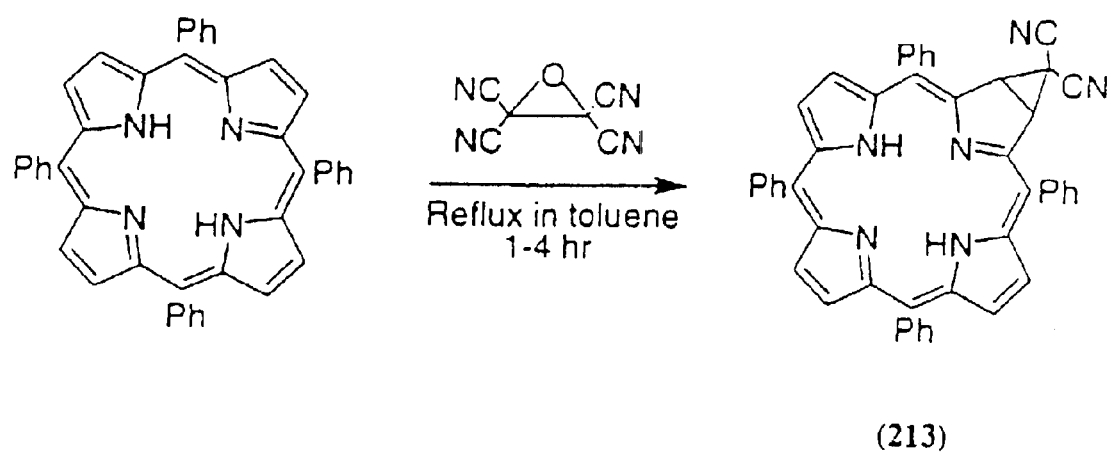
FIG. 3 shows the reaction of tetraphenylporphyrin with TCNEO to form a preferred intermediate, 5,10,15,20-tetraphenyl-2,3-(3'-dicyano)cyclopropano-2,3-chlorin, of the invention.

The reaction of TCNEO with tetraphenylporphyrin (TPP) in 1,2-dibromoethane produced two purple compounds after one hour of refluxing. Starting material recovery was quite high (48%) but may possibly be improved by longer reaction times. The least polar burgundy product was found to be the free base lactone chlorin, but the most polar compound (5,10,15,20-tetraphenyl-2,3-(3'-dicyano)cyclopropano-2,3-chlorin) was more interesting (see FIG. 3). Its absorption spectrum was chlorin-like with a Soret band at 416 nm and four Q bands at 518, 548, 586 and 642 nm with the Q band at 642 nm being the most intense. A parent ion at m/e=678 was observed by mass spectrometry. This is 64 units lower than expected for a TCNEO adduct. The proton NMR of this product indicated a high degree of symmetry with the P proton peaks at 8.7 ppm (d), 8.5 ppm (s) and 8.35 ppm (d). Additionally, a singlet integrating for 2 protons was observed at 6.85 ppm representing the pyrrolidine protons of the chlorin. High resolution mass spectrometry revealed the molecular formula of this compound to be $C_{47}H_{30}N_6$, suggesting that the compound contains a cyclopropyl moiety. This compound may have been used by Shea, et al. (Shea, K. M., et al. J. Chem. Soc.,Chem. Comm. 1998, 759), but no synthetic or experimental details were reported therein.

Figure 4:
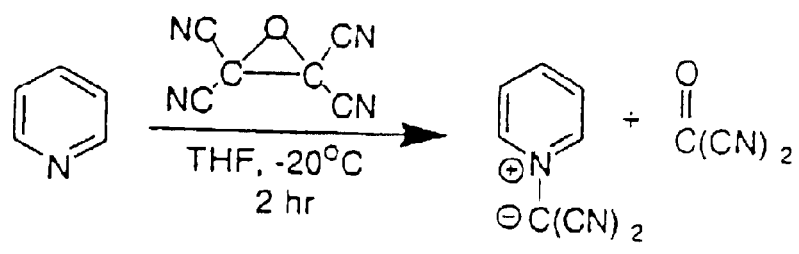
FIG. 4 shows the reaction of pyridine with TCNEO.

TCNEO may also be used to modify polypyrrolic macrocycles containing a tertiary nitrogen base, such as the CNC expanded porphyrins described in U.S. Pat. No. 5,726,304 and the family of "confused" porphyrin compounds. Other expanded porphyrins that may also be so modified are described in Sessler, *Expanded Contracted & Isomeric Porphyrins*, Pergamon: Oxford (1997). The underlying reaction is likely to involve the ability of TCNEO to fragment, as seen upon reaction with pyridine and other tertiary nitrogen bases (Linn, W. J., et al. J. Org. Chem. 1969, 34, 2146. One product of the reaction with pyridine is pyridinium dicyanomethylide as shown in FIG. 4 and the other product is presumed to be carbonyl cyanide.

Figure 5:
FIG. 5 shows the reaction of 5,15 diphenylporphyrin (DPP) with TCNEO and the production of two products (compounds 1 and 2).
Figure 5:
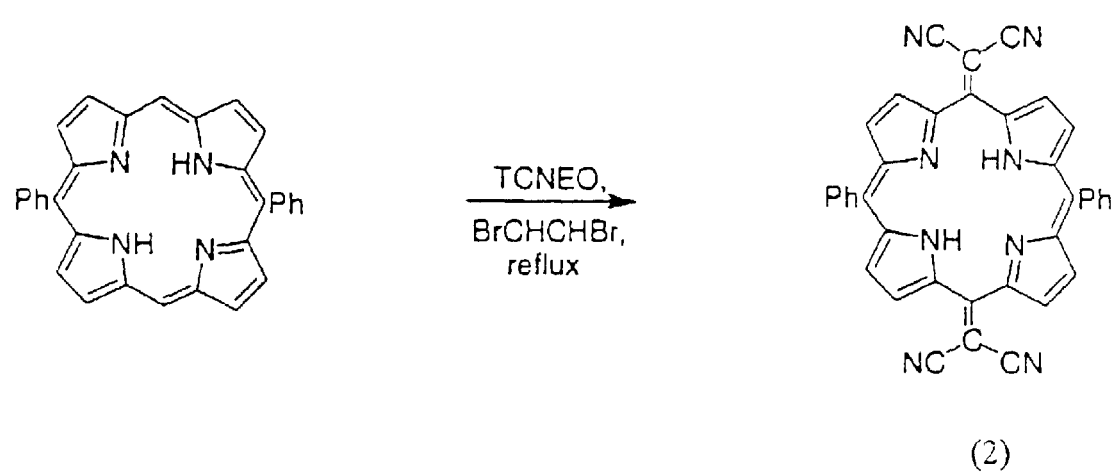

As 5,15-diphenylporphyrin (DPP) is known to be more reactive than tetraphenylporphyrins towards β addition reactions, such as osmium tetroxide mediated oxidation, the present inventors investigate the reaction between DPP and TCNEO. Reaction of 1.5 eq. TCNEO with DPP after refluxing in toluene for 3 hours produced two compounds: a red nonpolar compound 1 and a purple compound 2. See FIG. 5.

The absorbance spectrum of compound 1 product was very unusual with a split Soret at 376 and 416 nm and two intense overlapping Q bands at 510 and 534 nm. The proton NMR spectrum of this compound was quite different from that of the starting material. Two doublets at 6.5 ppm and 6.6 ppm, both integrating for 2 protons each, and a triplet at 7.1 ppm which integrated for 4 protons hinted that the molecule had lost its aromaticity but retained some sort of conjugation. Additionally, there were no peaks below 0 ppm to represent the NH protons. Instead there was a sharp singlet peak at 13.9 ppm which integrated for two protons. Protons on the nitrogen atoms of dipyrromethenes have previously been observed in this range. The protons of the two phenyl groups were observed at 7.4–7.5 as a large multiplet. Mass spectrometry of the red compound 1 revealed a compound at m/e 540 and with a molecular formula of $C_{35}H_{20}N_6O$. This corresponded to DPP plus $C_3ON_2$ and a loss of two protons.

Figure 6:
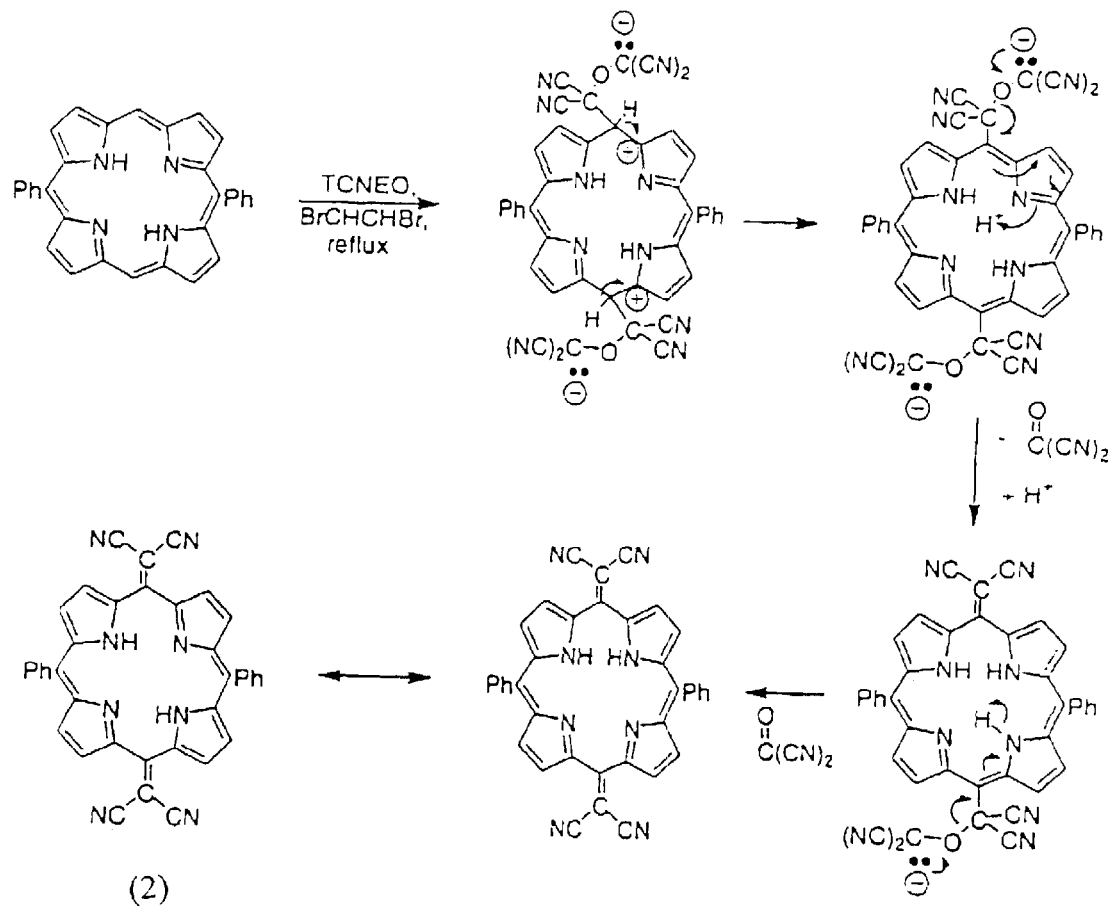
FIG. 6 shows a proposed scheme for the production of compound 2.

The purple compound 2 also displayed an unusual absorbance spectrum with one broad Soret band at 400 nm and one intense band at 562 nm. The proton NMR spectrum of the compound had a doublet representing four protons at 6.65 ppm, a doublet at 7.2 ppm also representing four protons, a multiplet representing the phenyl protons at 7.4–7.55 ppm and a singlet at 13.75 ppm representing two protons. The peaks at 6.65 and 7.2 ppm (both doublets with J=4.5 Hz) and the lack of splitting of the Soret and Q-band both indicated a higher degree of symmetry as compared to the red product compound 1. High resolution mass spectrometry determined the molecular formula of the parent ion at m/e 588 to correspond to a molecular formula of $C_{38}H_{20}N_8$. Without being bound by theory, the mechanism of formation of this compound presumably involves electrophilic aromatic substitution at the meso positions. A proposed scheme for the formation of compound 2 is shown in FIG. 6. Compound 1 may be formed by hydrolysis of compound 2.

Both compounds (1 and 2) may be considered intermediates for the produ tion of additional DPP derivatives since the cyano groups of compound 2 and the cyano and carbonyl groups of compound 1 are functionalities that may be readily modified further.

Figure 7:
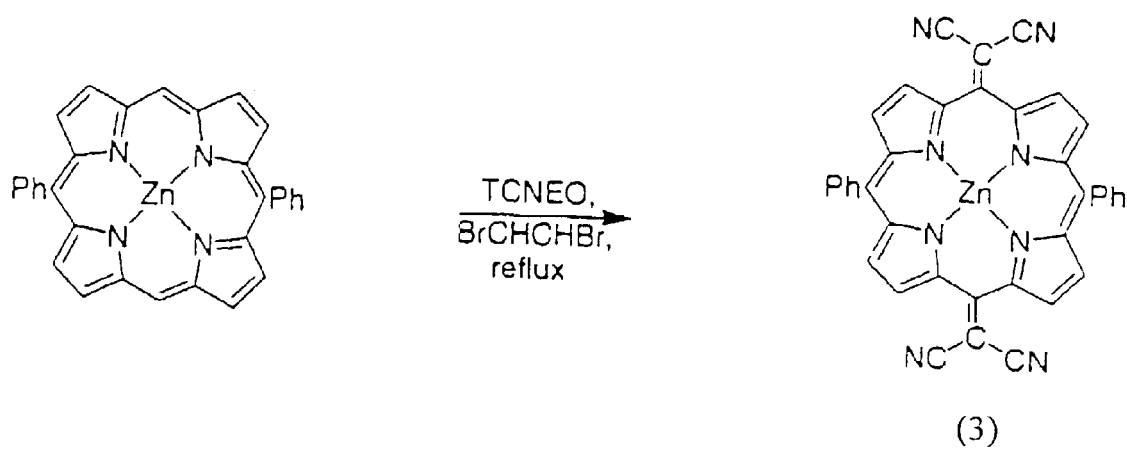
FIG. 7 shows the reaction of zinc metallated DPP with TCNEO to result in compound 3.

The metallated form of DPP may also be reacted with a carbonyl ylide. For example, after 3.6 equivalents of TCNEO and ZnDPP were refluxed for one hour in toluene, no starting material remained. See FIG. 7. After preparative TLC and isolation, the product compound 3 was analyzed.

The absorption spectrum of the compound was once again very unusual with a broad Soret band at 458 nm and an equally intense Q band at 638 nm. The proton NMR spectrum was similar to that observed for compound 2 formed in the reaction of TCNEO with free base DPP in that there were 2 doublets of equal integration at 6.5 and 7.1 ppm. High resolution mass spectrometry confirmed that compound 3 was indeed the zinc metallated analog of the purple compound 2 as the parent ion at m/e 650 corresponded to the molecular formula $C_{38}H_{18}N_8Zn$.

Figure 8:
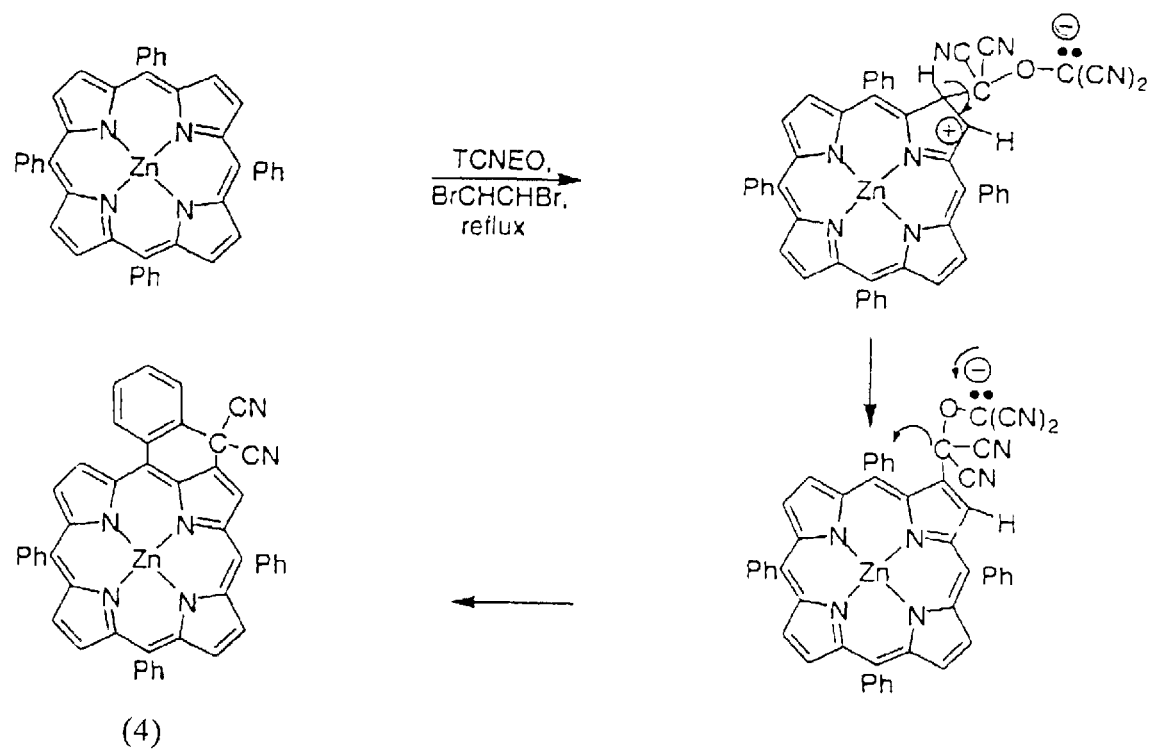
FIG. 8 shows the reaction of zinc metallated TPP with TCNEO to result in compound 4.

The corresponding reaction with metallated ZnTPP as the starting material resulted in the formation of a green product compound 4 (see FIG. 8). The compound displayed an absorption spectrum with a shoulder at 428 nm, a sharp Soret band at 442 and two Q bands at 584 and 638 nm. Low resolution mass spectrometry revealed a parent ion peak at m/e 738. High resolution mass spectrometry indicated this corresponded to a molecular formula of $C_{47}H_{26}N_6Zn$ which is one C(CN)2 fragment more and, once again, 2 protons fewer than the starting material. The proton NMR spectrum was very similar to that of the previously discussed monocyclized compounds derived from acid treatment of formylated TPPs. This characterization data led suggests cyclization of the dicyano moiety to produce compound 4.

Thus the present inventors have found that use of a carbonyl ylide in a 1,3-dipolar cycloaddition reaction provides an additional means for derivatizing polypyrrolic macrocycle photosensitizers beyond known Diels-Alder and osmium tetroxide mediated reactions. The cycloaddition reactions may be used with monophenyl-, diphenyl-, triphenyl-, and tetraphenyl- substituted polypyrrolic macrocycles. The methods of the invention permit the production of intermediates with reactive moieties at the β, β' and meso positions of polypyrrolic macrocycle, such as porphyrin, compounds.

The ability to generate new reactive intermediates such as 5,10,15,20-tetraphenyl-2,3-(3'-dicyano)cyclopropano-2,3-chlorin and compounds 1,2,3, and 4 has important consequences. First, the intermediates offer new approaches to the synthesis of new photoactive agents. Second, the reaction offers a new means of generating known photosensitizers that may be more economical or practical than previously known methods.

The new photosensitizers made possible by the invention include those encompassed by the formulas

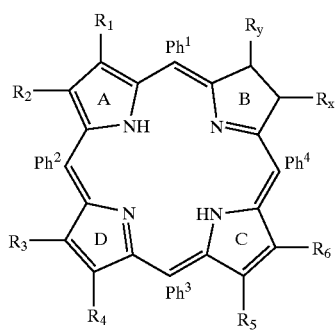

I

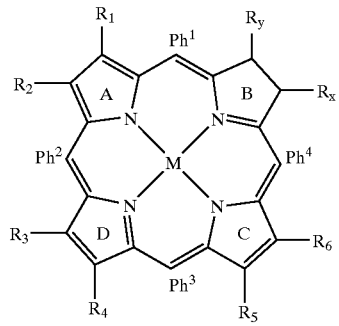

II wherein formula I represents the structure of a polypyrrolic macrocycle of the invention and formula II represents the structure of the metallated form of the macrocycle. M is a metal selected from the group consisting of Ni(II), Cu(II), Zn(II), Fe(III)Cl, Sn, Ge, Si, Ga, Al, Mn(III), Gd(III), In and Tc. Preferably, the metal is one which is either not toxic to higher organisms or readily removed or exchanged in favor of another, less toxic metal. Of course toxic metals remain encompassed by the invention for use in circumstances where the toxicity may be advantageously used to suppress the growth or proliferation of organisms, such as microorganisms.

$R_1$ through $R_6$ can be any one of a large number of ring substituents, so long as they do not interfere with the cycloaddition reaction outlined above. Preferably, $R_1$ through $R_6$ are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl; a carboxylic acid ester group, such as $-CH_2CH_2COOCH_3$, $-CH_2CH_2COOCH_2CH_3$, $-CH_2CH(CH_3)COOCH_2CH_3$, $-CH_2CH_2CH_2COOCH_2CH_3$, $-CH_2CH(CH_3)_2COOCH_2CH_3$; keto; hydroxy; nitro; amino; or the like. More preferably, the lower alkyl, alkyl carboxylic acid or acid ester group contains from 1 to about 8 carbon atoms, but more preferably, from 1 to about 6 or to about 4 or 3 carbon atoms.

Further, $R_1$ and $R_2$, $R_3$ and $R_4$, or $R_5$ and $R_6$, can be taken together with another ring, ring substituent or mesosubstituent to form a fused 5- or 6-membered ring. The fused 5- or 6-membered ring so formed may be any saturated or unsaturated, carbocyclic or heterocyclic 5- or 6-membered ring that does not interfere with the cycloaddition reaction of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when $R_1$ and $R_2$, $R_3$ and $R_4$, or $R_5$ and $R_6$, form a fused, 5- to 6-membered ring, the ring is a 6-membered ring. Most preferably, when $R_1$ and $R_2$, $R_3$ and $R_4$, or $R_5$ and $R_6$, form a ring, it is a 6-membered carbocyclic ring, i.e., a benzene ring.

In a particularly preferred embodiment, $R_1$ through $R_6$ are independently hydrogen, methyl, ethyl, or lower alkyl esters, most preferably being hydrogen, methyl or ethyl.

$R_x$ and $R_y$ are as defined above for $R_1$ through $R_6$.

$Ph^1$, $Ph^2$, $Ph^3$ and $Ph^4$ independently represent a group selected from H, substituted or unsubstituted alkyl groups, or substituted or unsubstituted aromatic rings, or substituted or unsubstituted cycloalkyl groups, which may be the same or different. Preferably, one or more of the $Ph^1$, $Ph^2$, $Ph^3$ and $Ph^4$ groups is not a phenyl group such that formulas I and II are directed to monophenyl-, diphenyl-, triphenyl-, and tetraphenyl- substituted polypyrrolic macrocycles When one or more of $Ph^1$, $Ph^2$, $Ph^3$ and $Ph^4$ is an alkyl group, they preferably have from about 1 to about 18 carbon atoms, more preferably about 1 to 12 carbon atoms and, even more preferably, about 1-6 carbon atoms. Examples of typical alkyl groups are methyl, ethyl, isopropyl, sec-butyl, tert-butyl, n-pentyl and n-octyl.

When one or more of $Ph^1$, $Ph^2$, Ph3 and $Ph^4$ is an alkyl group, it may be unsubstituted or substituted with any group that does not interfere with the cycloaddition or reduction reactions. For example, when one or more of $Ph^1$, $Ph^2$, $Ph^3$ and $Ph^4$ is an alkyl group may be substituted by a halogen atom, such as fluorine, chlorine or bromine; a hydroxy group, such as in pentoses and hexoses; thiol; or a carbonyl group, such as when the alkyl group is an aldehyde, ketone, carboxylic acid (e.g., a fatty acid) or ester or amide; a primary, secondary, tertiary, or quaternary amino group; nitrile; a phosphate group; a sulfonate group; and the like.

When one or more of $Ph^1$, $Ph^2$, $Ph^3$ and $Ph^4$ is a cycloalkyl group, it preferably contains from about 3 to about 7 carbon atoms. Examples of typical cycloalkyl groups include cyclopropyl, cyclohexyl, and cycloheteroalkyl, such as glucopyranose or fructofuranose sugars. When one or more of $Ph^1$, $Ph^2$, $Ph^3$ and $Ph^4$ is a cycloalkyl group, it may be unsubstituted or substituted with any group that does not interfere with the cycloaddition or reduction reactions. For example, when one or more of $Ph^1$, $Ph^2$, $Ph^3$ and $Ph^4$ is a cycloalkyl group, they may be substituted by any of the same substituents described above for the case when one or more of $Ph^1$, $Ph^2$, $Ph^3$ and $Ph^4$ is an alkyl group.

When one or more of $Ph^1$, $Ph^2$, $Ph^3$ and $Ph^4$ is an aryl group, it preferably contains from about 5 to about 12 carbon atoms, optionally containing one or more heteroatoms, and optionally including rings that are fused to the existing conjugated porphyrin ring structure. Examples of suitable aromatic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3, 4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3, 5-triazone, 1,2,4-triazine, 1,2,3-triazine, 1,2,4-oxazine, 1,3, 2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodianzine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine, steroidal compounds and the like.

In a particularly preferred embodiment, both $Ph^2$ and $Ph^4$ are phenyl groups.

In another embodiment, at least one of $Ph^1$, $Ph^2$, $Ph^3$ and $Ph^4$ has the structure:

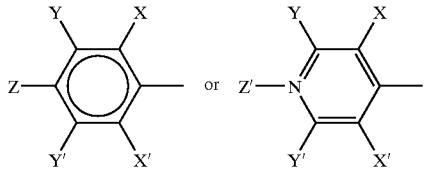

wherein X, Y, Z,X',Y' and Z' can be any one of a large number of substituents and are generally used to "fine tune" the biological activity, the biodistribution, the absorption and clearance characteristics, and the physical properties of the desired product. One way in which this may be done by selecting substituents in such a manner that the compound of formula (I) or (II) is an amphiphilic molecule. By "amphiphilic" is meant the molecule becomes more asymmetric, such as (1) having both (a) a highly polar, water-soluble region and (b) a highly hydrophobic, water-insoluble region; or (2) having both (a) a nonionic region and (b) an ionic region.

However, it should be noted that the invention also includes β,β'-dihydroxy meso-substituted chlorin, bacteriochlorin or isobacteriochlorin compounds having substantially or exactly identical aryl substituents. Further, any aryl substituent chosen should also have no adverse effect on the ability of the compound to undergo the cycloaddition reaction.

Preferably, X, X', Y, Y' and Z are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salt, such as —$CH_2COOH$, —$CH_2COO$—$Na^+$, —$CH_2CH(Br)COOH$, —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$C(CH_3)_2$—$COO^-K^+$, —$CH_2$—$CH_2$—$CH_2$—$CH_2$—$COOH$, $C(CH_3)_3$—$COOH$, $CH(Cl)_2$—$COOH$ and the like; (7) carboxylic acid ester, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_3$, —$CH_2CH(CH_3)_2COOCH_2CH_3$, and the like; (8) sulfonic acid or acid salt, for example, group I and group II salts, ammonium salts, and organic cation salts such as alkyl and quaternary ammonium salts; (9) sulfonic acid ester, such as methyl sulfonate, ethyl sulfonate, cyclohexyl sulfonate and the like; (10) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino)heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (11) cyano; (12) nitro; (13) a biologically active group; or (14) any other substituent that increases the amphiphilic nature of the compound of formula (I) or (II).

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-I-glucose; (6) O-methyl derivatives such as methyl I-glucoside, methyl J-glucoside, methyl I-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, L-gluconolactone, L-glucuronolactone, ascorbic acid, and dehydroascorbic acid; (10) phosphoric acid esters such as I-glucose 1-phosphoric acid, I-glucose 6-phosphoric acid, I-fructose 1,6-diphosphoric acid, and I-fructose 6-phosphoric acid; (11) deoxy sugars such as 2-deoxy-ribose, rhamnose (deoxy-mannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as I-amylose, amylopectin; dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Particularly useful examples of substituents tending to increase the amphiphilic nature of the compound of formula (I) include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) glycolipids, such as glycosyldiacylglycerols, cerebrosides, sulfate esters of cerebrosides or gangliosides.

In a preferred embodiment, X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, substituted or unsubstituted amino, cyano, nitro, or a biologically active group, and Z' is hydrogen or lower alkyl. In another embodiment, X, Y, X' and Y' are each hydrogen, and Z is selected from the group consisting of hydrogen, halogen, lower alkyl, lower alkoxy, hydroxy, carboxylic acid, carboxylic acid ester, sulfonic acid ester (especially aromatic sulfonic acid ester), nitro, amino (especially lower alkyl amino), cyano, and a biologically active group.

In yet another embodiment, X, Y, Z, X' and Y' are selected from the group consisting of hydrogen, methyl, ethyl, t-butyl, methoxy, hydroxy, OR where R is an alkyl group or a fatty acid group having from 6 to 18 carbon atoms, fluoro, chloro, iodo, bromo, —C(O)—$OCH_3$, cyano, nitro, or a ligand specific for a biological receptor. In a further preferred embodiment, X, X', Y and Y' and Z is selected from the group consisting of hydrogen, halogen, lower alkyl, lower alkoxy, hydroxy, carboxylic acid or acid salt, carboxylic acid ester, sulfonic acid ester, sulfonic acid or acid salt, nitro, amino, cyano, and a biologically active group. In still another preferred embodiment, at least one of X, Y, Z, X' and Y' is a biologically active group or a substituent that increases the amphiphilic nature of the molecule.

Particularly preferred specific examples of groups that can serve as one or more of $S^1$ through $S^4$ include the following:

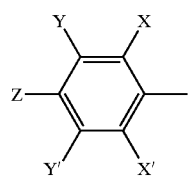

| X | X' | Y | Y' | Z |
|---|----|---|----|---|
| —H | —H | —H | —H | —H |
| —OH | —H | —H | —H | —H |

-continued

| | | | | |
|---|---|---|---|---|
| —H | —H | —OH | —H | —H |
| —H | —H | —H | —H | —OH |
| —H | —H | —OH | —OH | —OH |
| —H | —H | —H | —H | —SO₃H(Na) |
| —CH₃ | —CH₃ | —H | —H | —CN |
| —H | —H | —OCH₃ | —OCH₃ | —OCH₃ |
| —H | —H | —H | —H | —COOH(Na) |
| —H | —H | —COOH(Na) | —COOH(Na) | —H |
| —H | —H | —H | —H | —C₆H₁₂COOH(Na) |
| —H | —H | —H | —C₆H₁₂COOH(Na) | —H |
| —H | —H | —C₆H₁₃ | —H | —SO₃H(Na) |
| —H | —H | —H | —COOH(Na) | -tert-Butyl |
| —H | —CH₂NH₂ | —H | —H | —H |
| —H | —H | —H | —H | —NH₂ |
| —OH | —H | —H | —H | —CH₂NH₂ |
| —H | —H | —H | —H | —C₄H₈NH₂ |
| —H | —H | —H | —COOCH₃ | —COOH(Na) |
| —OH | —H | —H | —COONHCH₃ | —H |
| —H | —H | —H | —COONHCH₃ | —COOH(Na) |
| —H | —H | —H | -imidazoyl | —H |
| —H | —H | —H | -glycinyl | —H |
| —H | —H | —H | -steroidyl | —H |
| —H | —H | —H | -glycosyl | —H |
| —H | —H | —H | —H | -imidazoyl |
| —H | —H | —H | —H | -glycinyl |
| —H | —H | —H | —H | -steroidyl |
| —H | —H | —H | —H | -glycosyl |

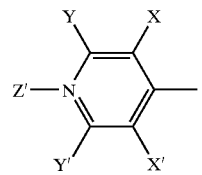

| X | X' | Y | Y' | Z |
|---|---|---|---|---|
| —H | —H | —H | —H | —H |
| —H | —H | —H | —H | —CH₃ |
| —H | —H | —H | —H | —C₆H₁₂OH |
| —H | —H | —H | —OH | —H |
| —H | —H | —OH | —H | —H |
| —H | —H | —H | —COONHCH₃ | —H |
| —H | —H | —H | —H | -benzyl |
| —H | —H | —H | —C₆H₁₂OH | —CH₃ |
| —H | —H | —C₆H₁₃ | —H | —CH₃ |

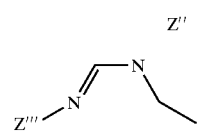

| Z'' | Z''' |
|---|---|
| —H | —H |
| —CH₃ | —H |
| —H | —CH₃ |
| —H | —C₆H₁₂ |
| —C₆H₁₂ | —H |

The present invention also includes the intermediates produced by the cycloaddition reaction and represented by the formula

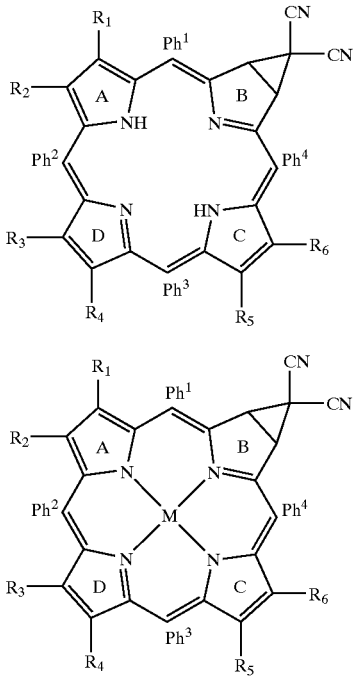

wherein all variable positions are as defined above for formulas I and II.

In a particularly preferred aspect of the invention, derivatives are produced in such a manner that the polypyrrolic macrocyclic compound to be made will be an amphiphilic molecule. By "amphiphilic" is meant that the molecule has become more asymmetric, such as (1) having both (a) a highly polar water-soluble region and (b) a highly hydrophobic, water-insoluble region;

(2) having both (a) a non-ionic region and (b) an ionic region; or (3) having both (a) an anionic portion and (b) a cationic portion.

The derivative polypyrrolic. macrocycle compounds of the invention are preferably made by derivatizing an intermediate compound produced by a 1,3-dipolar cycloaddition to the corresponding polypyrrolic macrocycle. Such a cycloaddition reaction may be conducted by a method comprising contacting a polypyrrolic macrocycle with a 1,3-dipole compound in a suitable solvent and and refluxed. Preferably, the macrocycle is a photosensitizer or a photosensitizer precursor compound. The method is preferably conducted with a carbonyl ylide as the dipole. More preferred is the use of TCNEO as the carbonyl ylide. The ratio of the macrocycle to dipole is preferably about 1:1 to about 1:3, more preferably about 1:1 or about 1:1.5.

Appropriate solvents for use in the practice of the invention are any one of a wide variety of organic solvents that is capable of dissolving at least one of the reactants and, yet, does not interfere with the course of the reaction to any significant degree. Preferably, such a solvent should also have a boiling point sufficiently low to evaporate off after the reaction is completed. Examples of such solvents include alcohols, such as methanol, ethanol, α-propanol, n-butanol, 2-ethylhexanol, benzyl alcohol, and glycerol; ethers such as diethyl ether, n-butyl ether and dimethoxyethane; aromatic solvents, such as benzene, toluene, and aniline; ketones such as acetone and methyl ethyl ketone; esters such as ethyl acetate, butyl acetate, and ethyl benzoate; and chlorinated solvents such as carbon tetrachloride, chloroform, dichloromethane, 1,1,1-trichloroethane, and combinations thereof. Preferred solvents include 1,2-dibromoethane, toluene, or THF.

Following the reflux, the solvent may be removed by any conventional means, including evaporation under reduced pressure or vacuum, and the resultant products isolated. Any isolation or preparative method may be used to obtain the product compounds, including thin layer chromatography (TLC) or any other chromatographic means, including high performance liquid chromatography (HPLC).

In a preferred embodiment, the reaction takes place under an inert atmosphere to avoid oxidation or oxidative polymerization of the components. When used, the inert atmosphere is usually provided by forming a protective blanket of an inert gas, such as argon, helium, or $N_2$, over the reaction mixture or bubbling an inert gas through it. Other methods of providing an inert atmosphere include performing the reaction under reduced pressure to form an atmosphere of solvent vapor(s).

The reaction temperature in the reaction can vary widely depending on the reactivity of the reactants. However, the temperature should not be so high as to decompose the reactants or so low as to cause inhibition of the condensation or freezing of the solvent. In most cases, the reaction can take place at a temperature ranging from about room temperature, for reasons of convenience, to the reflux temperature of the reaction mixture, which typically varies from about 25 to about 150° C.

The time required for the reaction will depend to a large extent on the temperature being used and the relative reactivities of the starting materials. Particularly when the meso-substituents are aryl, cycloalkyl, or a bulky alkyl group such as tert-butyl, the time required for the reaction may increase due to steric hindrance. Therefore, the reaction time can vary greatly, for example, from about five minutes to about two days. Typically, the time required may be from about 1 to about 24 hours, preferably from about 1 to about 18 hours, and more preferably from about 1 to about 2, about 3 or about 4 hours.

At the conclusion of the evaporation step (b), a residue remains, from which the meso-disubstituted tripyrrane can be isolated by any conventional means, such as by chromatography, crystallization, re-crystallization, sublimation, various combinations of these methods, and the like. Typically, two primary types of impurities must be removed from the residue: (1) high molecular weight polymeric materials; and (2) the dipyrromethane molecule corresponding to the desired tripyrrane product, which occurs as a by-product of the above-described reaction.

The cyano containing intermediate compounds produced by the above methods may be reduced to produce amine groups for further derivatization of the compounds. In a preferred embodiment of the invention, lithium aluminum hydride is used for the reduction, but any suitable reducing agent known in the art may be used for reducing the compound.

The derivative compounds made possible by the invention are useful as photosensitizers used in photodynamic therapy (PDT) and as synthetic intermediates for making related photosensitizers. Specifically, these photosensitizers are useful in sensitizing neoplastic cells or other abnormal tissues to destruction by irradiation with visible light. Upon photoactivation; the energy of photoactivation is believed to be transferred to endogenous oxygen, thus converting it to singlet oxygen. This singlet oxygen is thought by some to be responsible for the observed cytotoxic effect. Alternatively, there may be direct electron transfer from the photoactivated molecule. The method of van Lier, *Photobiological Techniques*, 216, 85–98 (Valenzo et al. eds. 1991) can be used to confirm the ability of any given compound to generate singlet oxygen effectively, thus making it a good candidate for use in photodynamic therapy. In addition, the photoactivated forms of porphyrin are able to fluoresce, and this fluorescence can aid in imaging a tumor.

Alternatively, 1,3-diphenylisobenzofuran (DPBF) may be used as a chemical quencher to determine the singlet oxygen quantum yields of various potential PDT agents. 186 Monitoring the absorption decay of the absorption band at 415 nm (that of DPBF in DMF using UV-Visible spectrophotometry) in the presence of our compounds and during irradiation with visible light confirmed the production of singlet oxygen.

Typical indications known in the art include diagnosis and destruction of tumor tissue in solid tumors, such as those of bronchial, cervical, esophageal or colon cancer; dissolution of plaques in blood vessels (see, e.g., U.S. Pat. No. 4,512, 672, which is hereby incorporated by reference); treatment of topical conditions such as acne, athlete's foot, warts, papilloma and psoriasis; and treatment of biological products, such as blood for transfusion to eliminate infectious agents.

Additionally, when metals such as In or Tc are used, the metallated pigment compounds of the invention have diagnostic use in nuclear medicine. Similarly, when M is Mn(III) or Gd(III), the compounds may be useful in magnetic resonance imaging. These are also applications where, due the variability possible with,respect to the substitution patterns, significantly improved biodistribution properties may be achieved by using the compounds of the invention.

The photosensitizers made from the compounds of the invention can be formulated into pharmaceutical compositions for administration to the subject or applied to an in vitro target using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures.

Generally, for the diagnosis or treatment of solid tumors, the compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as-wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the photosensitizer compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

In addition to in vivo use, the compounds made from the intermediate compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

Having now generally described the invention, the same will be more readily understood through reference to the following examples which are provided by way of illustration, and are not intended to be limiting of the present invention, unless specified.

EXAMPLE 1

Preparation of 5,10,15,20-Tetraphenyl-2,3-(3'-dicyano)cyclopropano-2,3-chlorin:

A solution of 5,10,15,20-tetraphenylporphyrin (50 mg, 0.08 mmol) and tetracyanoethylene oxide (TCNEO) (50 mg, 0.34 mmol) in 1,2-dibromoethane (2 mL) was refluxed for 1 hour. The solvent was evaporated in vacuo, and preparative TLC performed (silica; 1:1 hexane:chloroform).

RF 0.7 (silica—1% MeOH:CHCl$_3$); 1H-NMR (400 MHz, CDCl$_3$)=6.85 (s, 2H), 7.80 (m, 8H), 7.87 (m, 4H), 7.99 (d, J=7.47 Hz, 2H), 8.09 (d, J=6.72 Hz, 2H), 8.20 (m, 2H), 8.35 (d, J=7.16 Hz, 2H), 8.38 (d, J=4.99 Hz, 2H), 8.51 (s, 2 H), 8.70 (d, J=4.84 Hz, 2 H). UV-Vis (CH$_2$C$_2$) max 416, 514, 554, 586, 642 nm; MS (EI) m/e calc'd for C$_{47}$H$_{30}$N$_6$: 678.25317, found 678.25190 (M+, 100%).

EXAMPLE 2

Preparation of Compounds 1 and 2

A solution of DPP (16 mg, 0.035 mmol) and tetracyanoethylene oxide (TCNEO) (7.5 mg, 0.05 mmol) in 1,2-dibromoethane (5 mL) was refluxed for 3 hours. The solvent was evaporated in vacuo, and preparative TLC performed (silica; 1:1 toluene:hexane) to yield compounds 1 and 2.

Compound 1

RF 0.8 (silica—CHCl$_3$); IR 2210(s), 1729.8 (m), 1571.7 (s), 1509 (m), 1384 (m), 1182 (s) cm-1 1H-NMR (400 MHz, CDCl$_3$)=6.5 (d, J=4.41 Hz, 2H, H), 6.6 (d, J=4.29 Hz, 2H, H), 7.14 (t, J=3.95 Hz, 4H, H), 7.4–7.55 (m, 10H), 13.9 (s, 2H); UV-Vis (CH$_2$Cl$_2$) max=376, 416, 510, 534 nm; MS (EI) m/e calc'd for C$_{35}$H$_{20}$ON$_6$: 540.16986, found 540.17000 (M+, 100%); yield 36%.

Compound 2

RF 0.6 (silica—CHCl$_3$); IR 2215 (s), 1650 (m), 1567 (m) cm-1 1H-NMR (400 MHz, CDCl$_3$)=6.65 (d, J=4.63 Hz, 4H, H), 7.19 (d, J=4.47 Hz, 4H, H), 7.4–7.58 (m, 10H), 13.75 (s, 2H);UV-Vis (CH$_2$C$_2$) max=400, 562 nm; LRMS (EI) m/e 588 (M+, 100%), 563 (M+-CN, 40%); HRMS (EI) m/e calc'd for C$_{38}$H$_{20}$N$_8$: 588.18109, found 588.18193 (M+, 100%); yield 45%.

EXAMPLE 3

Preparation of Compound 3

A solution of ZnDPP (50 mg, 0.07 mmol) and tetracyanoethylene oxide (TCNEO) (19 mg, 0.13 mmol) in 1,2-dibromoethane (5 mL) was refluxed for 2 hours. The solvent was evaporated in vacuo, and preparative TLC performed (silica; chloroform).

RF 0.6 (silica—1% MeOH:CHCl$_3$); IR 2213.8(s), 1563.9 (m), 1492 (s) cm-1 1H-NMR (400 MHz, CDCl3) 6.45 (d, J=4.40 Hz, 4H, H), 7.03 (d, J=4.41 Hz, 4H, H);UV-Vis (CH$_2$Cl$_2$) max 420(sh), 458, 638 nm; LRMS (EI) m/e 650 (M+, 100%), 625 (M+-CN, 80%), 602 (60%); HRMS (EI) m/e calc'd for C$_{38}$H$_{18}$N$_8$Zn: 650.09460, found 650.09565 (M+, 100%).

EXAMPLE 4

Preparation of Compound 4

A solution of ZnTPP (91 mg, 0.13 mmol) and tetracyanoethylene oxide (TCNEO) (73 mg, 0.51 mmol) in 1,2-dibromoethane (2 mL) was refluxed for 24 hours. The solvent was evaporated in vacuo, and preparative TLC performed (silica; chloroform).

RF 0.5 (silica—1% MeOH:CHCl$_3$); IR (cm-1) 2227 (m), 1743 (s), 1592 (m), 1437 (s), 1271 (s); UV-Vis (CH$_2$C$_2$) max=428(sh), 442, 548, 638 nm 1H-NMR (400 MHz, CDCl$_3$)=7.6 (t, 2H), 7.7–7.8 (m, 8H), 7.86 (t, 1H), 8.10–8.20 (m, 6H), 8.38 (d, J=7.24 Hz, 1H), 8.55 (d, J=7.36 Hz, 1H), 8.80 (m, 4H, H), 8.95 (d, J=4.64 Hz, 1H, H), 9.2 (s, 1H, 'H), 9.65 (d, J=4.72 Hz, 1H, H); MS (EI) m/e calc'd for C$_{47}$H$_{26}$N$_6$Zn: 738.15106, found 738.15237 (M+, 100%).

All references cited herein are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A method of modifying a polypyrrolic macrocycle, said method comprising reacting said macrocycle with a carbonyl ylide capable of forming a cyano containing macrocycle under refluxing conditions to produce a cyano containing compound, and reducing a cyano group of said compound with a reducing agent to produce an amine group.

2. The method of claim 1 wherein said carbonyl ylide is tetracyanoethylene oxide (TCNEO).

3. The method of claim 1 wherein said macrocycle is a photosensitizer.

4. The method of claim 3 wherein said photosensitizer is a porphyrin.

5. The method of claim 4 wherein said porphyrin is a tetraphenylporphyrin (TPP) or a diphenylporphyrin (DPP).

6. The method of claim 1 wherein said reducing agent is lithium aluminum hydride.

7. A method of modifying a polypyrrolic macrocycle, said method comprising reacting said macrocycle with a carbonyl ylide capable of forming a cyano containing macrocycle under refluxing conditions to produce a cyano containing compound, and hydrolyzing a cyano group of said compound to produce an acid or carboxylate moiety.

8. The method of claim 7 further comprising derivatization of said acid or carboxylate moiety to be an ester, amide, or thioamide.

9. The method of claim 7 wherein said carbonyl ylide is tetracyanoethylene oxide (TCNEO).

10. The method of claim 7 wherein said macrocycle is a photosensitizer.

11. The method of claim 10 wherein said photosensitizer is a porphyrin.

12. The method of claim 11 wherein said porphyrin is a tetraphenylporphyrin (TPP) or a diphenylporphyrin (DPP).

13. The method of claim 1 wherein said cyano containing compound has a structure represented by one of formulas III, IV, (1), (2), (3) or (4) below

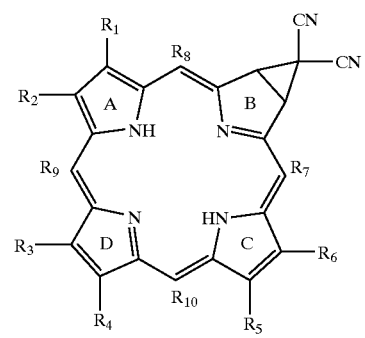

III

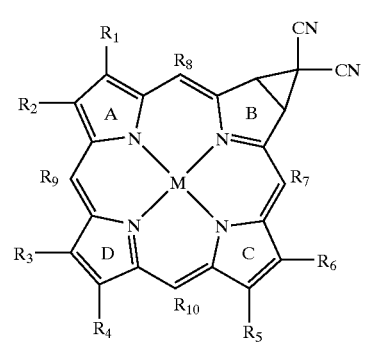

IV

-continued (1)
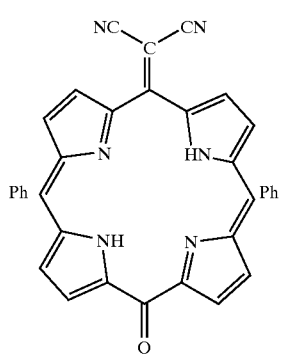

(2)
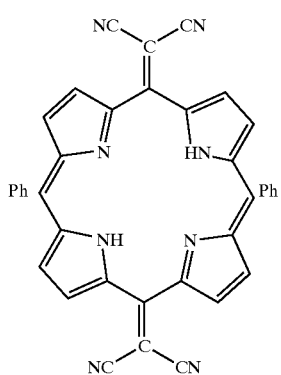

(3)
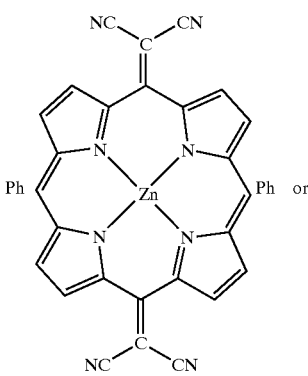

(4)
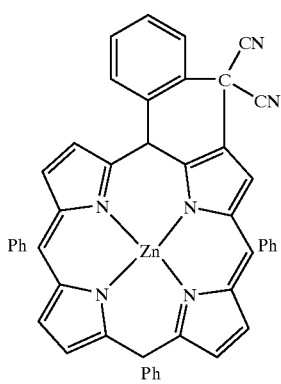

wherein
M is a metal selected from the group consisting of Ni(II), Cu(II), Zn, Sn, Ge, Si, Ga, Al, Mn(III), Gd(III), In and Tc;

$R_1$ through $R_6$ are independently a hydrogen atom, a lower alkyl group, a lower alkyl carboxylic acid or acid ester group, keto, hydroxy, nitro, amino, or a group that, taken together with another pyrrolic ring, ring substituent or meso-substituent, forms a fused 5- or 6-membered ring; and each of $R_7$ through $R_{10}$ is independently selected from H, substituted or unsubstituted alkyl groups, or substituted or unsubstituted aromatic rings, or substituted or unsubstituted cycloalkyl groups, which may be the same or different; and Ph is phenyl.

14. The method of claim 7 wherein said cyano containing compound has a structure represented by one of formulas III, IV, (1), (2), (3) or (4) below III
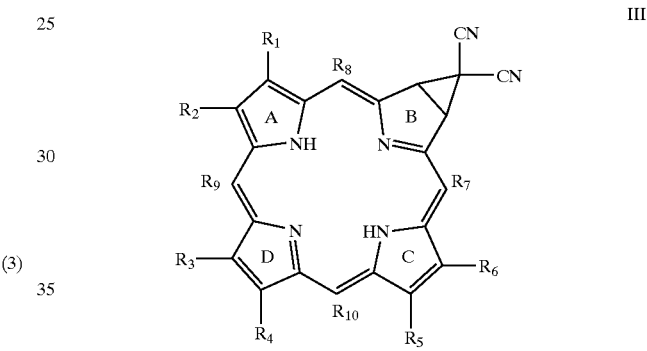

IV
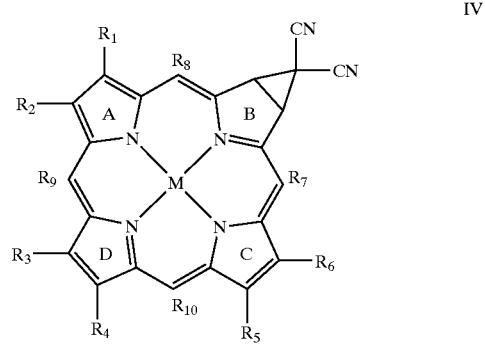

(1)
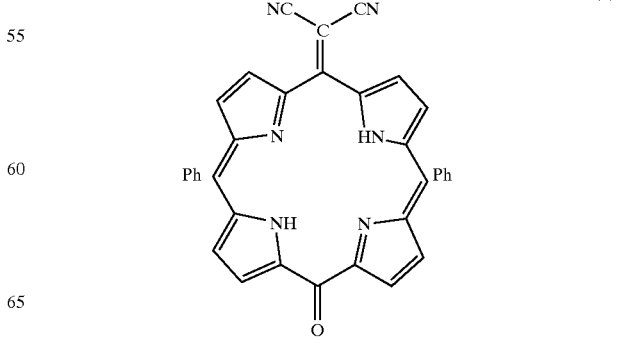

-continued (2)
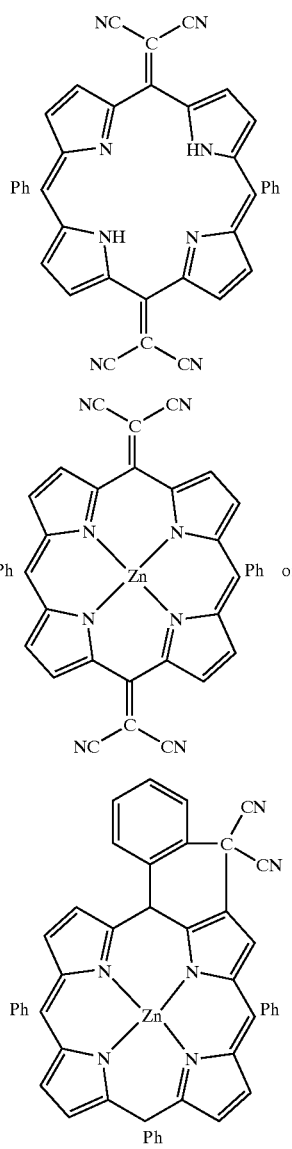

(3)
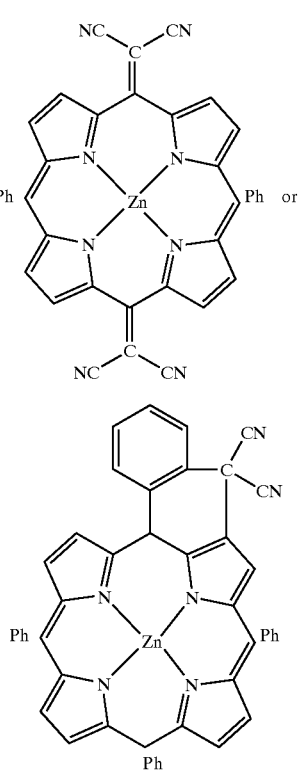

(4)
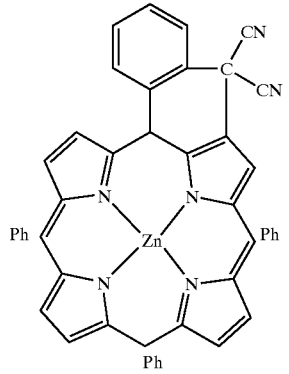

wherein
  M is a metal selected from the group consisting of Ni(II), Cu(II), Zn, Sn, Ge, Si, Ga, Al, Mn(III), Gd(III), In and Tc;
  $R_1$ through $R_6$ are independently a hydrogen atom, a lower alkyl group, a lower alkyl carboxylic acid or acid ester group, keto, hydroxy, nitro, amino, or a group that, taken together with another pyrrolic ring, ring substituent or meso-substituent, forms a fused 5- or 6-membered ring; and
  each of $R_7$ through $R_{10}$ is independently selected from H, substituted or unsubstituted alkyl groups, or substituted or unsubstituted aromatic rings, or substituted or unsubstituted cycloalkyl groups, which may be the same or different; and
  Ph is phenyl.

15. A compound produced by the method of claim 1.
16. A compound produced by the method of claim 6.
17. A compound produced by the method of claim 7.
18. A compound produced by the method of claim 8.
19. The compound of claim 16 having a structure represented by one of the following formulas

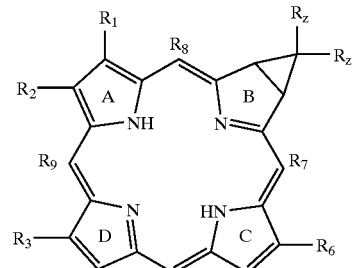

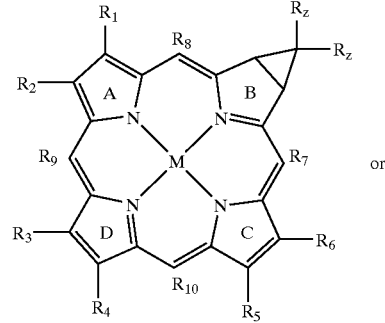
or

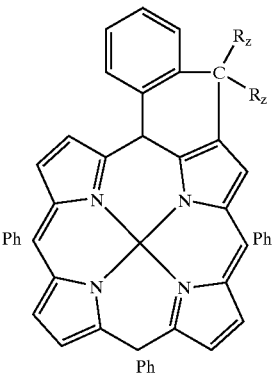

wherein
  M is a metal selected from the group consisting of Ni(II), Cu(II), Zn, Sn, Ge, Si, Ga, Al, Mn(III), Gd(III), In and Tc;
  $R_1$ through $R_6$ are independently a hydrogen atom, a lower alkyl group, a lower alkyl carboxylic acid or acid ester group, keto, hydroxy, nitro, amino, or a group that, taken together with another pyrrolic ring, ring substituent or meso-substituent, forms a fused 5- or 6-membered ring; and
  each of $R_7$ through $R_{10}$ is independently selected from H, substituted or unsubstituted alkyl groups, or substituted or unsubstituted aromatic rings, or substituted or unsubstituted cycloalkyl groups, which may be the same or different; and
  Ph is phenyl and —$R_z$ is —CN where one or more —$R_z$ is —CH$_2$NH$_2$ resulting from reduction of said —CN.

20. The compound of claim 17 having a structure represented by one of the following formulas

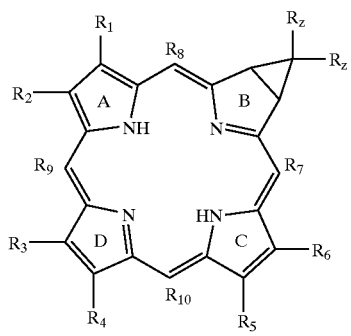

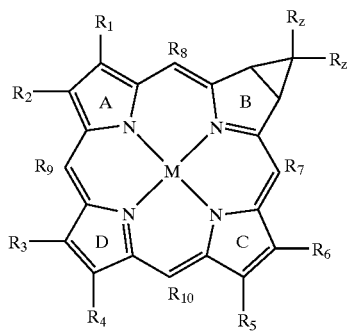

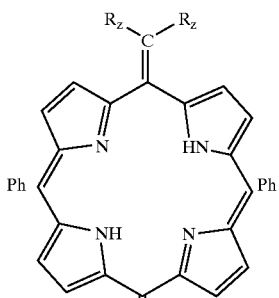

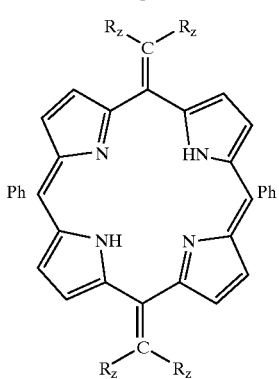

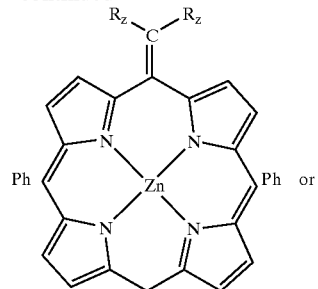

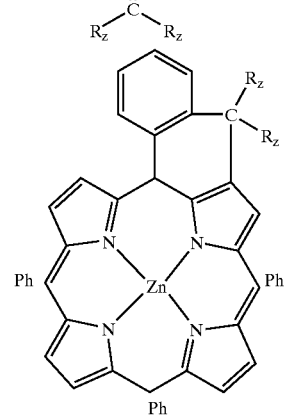

wherein

M is a metal selected from the group consisting of Ni(II), Cu(II), Zn, Sn, Ge, Si, Ga, Al, Mn(III), Gd(III), In and Tc;

$R_1$ through $R_6$ are independently a hydrogen atom, a lower alkyl group, a lower alkyl carboxylic acid or acid ester group, keto, hydroxy, nitro, amino, or a group that, taken together with another pyrrolic ring, ring substituent or meso-substituent, forms a fused 5- or 6-membered ring; and each of $R_7$ through $R_{10}$ is independently selected from H, substituted or unsubstituted alkyl groups, or substituted or unsubstituted aromatic rings, or substituted or unsubstituted cycloalkyl groups, which may be the same or different; and Ph is phenyl and —$R_z$ is —CN where one or more —$R_z$ is —COOH resulting from hydrolysis of said —CN.

* * * * *